United States Patent [19]
Johnson

[11] Patent Number: 5,290,518
[45] Date of Patent: Mar. 1, 1994

[54] FLEXIBLE EXTRACTION DEVICE WITH BURSTABLE SIDEWALL

[75] Inventor: Randall S. Johnson, Fairport, N.Y.

[73] Assignee: Eastman Kodak Company, Rochester, N.Y.

[21] Appl. No.: 5,686

[22] Filed: Jan. 19, 1993

Related U.S. Application Data

[63] Continuation-in-part of Ser. No. 931,231, Aug. 17, 1992, abandoned.

[51] Int. Cl.$^5$ .................. G01N 31/22; G01N 33/50
[52] U.S. Cl. .................. 422/58; 422/61; 422/101; 422/102; 436/177; 436/178; 436/180
[58] Field of Search .................. 422/58, 61, 100, 101, 422/256, 102; 436/177, 178, 180; 73/863.71

[56] References Cited

U.S. PATENT DOCUMENTS

Re. 29,725  8/1978  Johnson et al. .
2,932,385  4/1960  Bollmeier et al. .
3,799,742  3/1974  Coleman .
4,065,263  12/1977  Woodbridge, III .
4,458,811  7/1984  Wilkinson .................. 206/219
4,965,047  10/1990  Hammond .................. 422/58

FOREIGN PATENT DOCUMENTS 666329    7/1963  Canada .
381501    2/1990  European Pat. Off. .
WO 86/00704  1/1986  PCT Int'l Appl. .

Primary Examiner—Jill A. Johnston
Attorney, Agent, or Firm—Dana M. Schmidt

[57]  ABSTRACT

A device and method are disclosed for conducting a reaction, such as an extraction reaction. The device is flexible and provides contained compartments with pre-incorporated liquids. The liquids are reliably moved past temporary barriers by constructing the barrier to be a relatively thin sheet that bursts preferentially compared to seals between the sheet and the rest of the material defining the compartments.

14 Claims, 6 Drawing Sheets

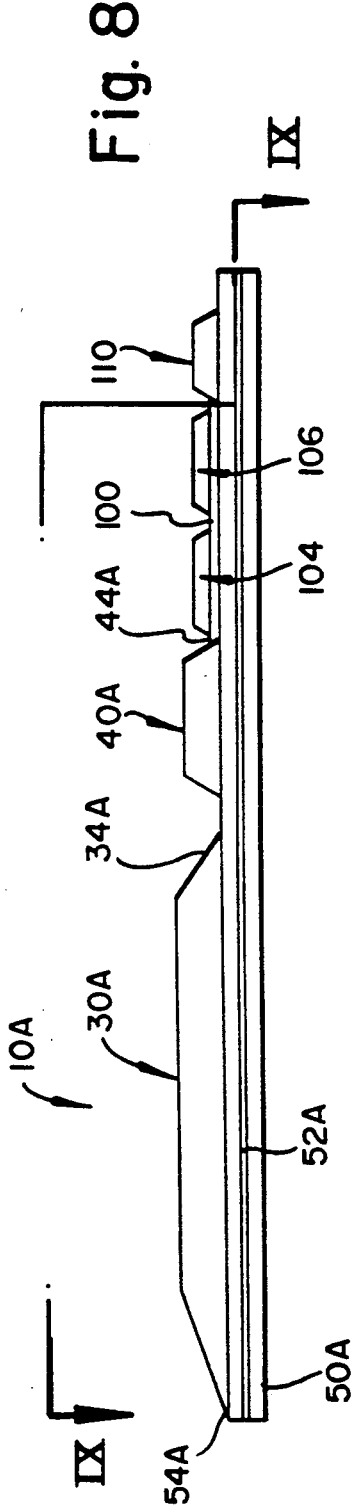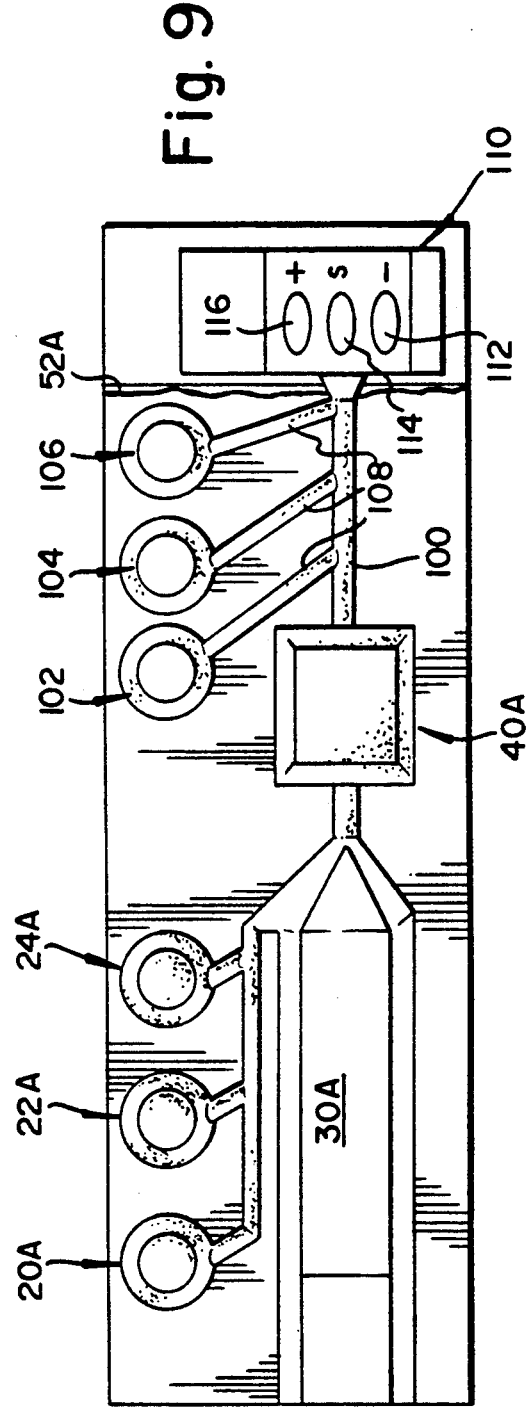

FLEXIBLE EXTRACTION DEVICE WITH BURSTABLE SIDEWALL

RELATED APPLICATIONS

This is a continuation-in-part application of U.S. Ser. No. 931,231 filed on Aug. 17, 1992 and now abandoned.

FIELD OF THE INVENTION

The invention relates to flexible reaction devices which move liquids by bursting them through temporary barriers.

BACKGROUND OF THE INVENTION

Reaction cuvettes have been provided in the past with a burstable reagent compartment, a reaction flow passage between the inlet end and exit aperture, and a filter across the flow passage. Examples can be found, e.g., in WO 86/00704. However, the cuvette in the latter operates by bursting the seal between the two sheets defining the reagent compartment, rather than by bursting the container wall. Such a construction is also used in other cuvettes having burstable compartments, e.g., those described in U.S. Pat. Re. No. 29,725 and EPA 381501.

Such burstable seals can produce problems of indeterminate sealing strength. That is, the force needed to burst the seal is not uniformly the same from cuvette to cuvette, due to variances in the sealing conditions (bonding temperatures and/or pressures). As a result, the temporary seal can fail unexpectedly or prematurely, leading to unsatisfactory results.

Therefore, there has been a need prior to this invention to provide such a cuvette wherein the burst strength of the compartment is more predictable and uniform.

SUMMARY OF THE INVENTION

I have constructed an extraction device that solves the above-mentioned problem by ensuring that bursting occurs through a sidewall that is part of the burstable compartment, rather than a seal. Such sidewalls have burst strengths that are more easily controlled in manufacturing than the burst strength of the seals.

More specifically, in accordance with one aspect of the invention, there is provided a generally flexible extraction device containing a predisposed reactant, comprising first and second plastic sheets superimposed and sealed together by first seal means to comprise a spaced compartment, a reagent in the compartment, the second sheet being thinner and more burstable than the first sheet so as to allow fracturing of the compartment through the second sheet at a predictable force, a third plastic sheet attached by second seal means to the first two sheets with the second sheet being between, and generally parallel to, the first and third sheets, the third sheet being formed so as to be spaced away from the first and second sheets adjacent to the compartment and to comprise a reaction chamber and inlet means for introducing a specimen between the third and second sheets to the reaction chamber, an exit aperture, and a flow path for liquid extending between the second and third sheets and between the inlet means and the exit aperture, a filter extending across the flow path between the first and third sheets, and third seal means across the flow path in between the filter and the compartment, formed between the second and third sheets so as to temporarily isolate the filter from liquid flowing out of the reaction chamber, each of the seal means being stronger than the burst strength of the second sheet.

In accordance with another aspect of the invention, there is provided a method of bursting a burstable compartment in an extraction device to advance a liquid comprising the steps of sealing a liquid within a compartment defined by sidewalls sealed together at seals along the perimeter of the compartment to temporarily confine the liquid, and then applying external pressure sufficient to burst the liquid out of the compartment but not out of the device. The method is improved in that it includes providing as one of the sidewalls, a sheet material substantially thinner than the material of other of the sidewalls and with a thinness sufficient to cause the one sidewall to burst under the pressure before the seals burst, so that the bursting occurs predictably through the one sidewall at a predetermined burst force, and not through the seals.

Accordingly, it is an advantageous feature of the invention that an extraction device is provided with burstable compartments, the bursting of which is more readily predictable than has been the case in prior art devices.

It is a further advantageous feature of the invention that such an extraction device can be integrated with a detection compartment, all in one integral device.

Other advantageous features will become apparent upon reference to the following Detailed Description, when read in light of the attached drawings.

DETAILED DESCRIPTION OF THE DRAWINGS

FIG. 8 is a side elevation of an alternate form of the invention;

FIG. 9 is a section view taken along the line IX—IX of FIG. 8;

DETAILED DESCRIPTION OF THE INVENTION

The invention is described in connection with the preferred embodiments, in which the device is used to extract antigens from biological materials, using pre-incorporated extracting reagents, the device having compartments formed by heat-sealing certain flexible plastic materials. In addition, the invention is applicable regardless of the kind of reagent that is pre-incorporated, and regardless of the method of sealing or the flexible materials that are used.

Figure 1:
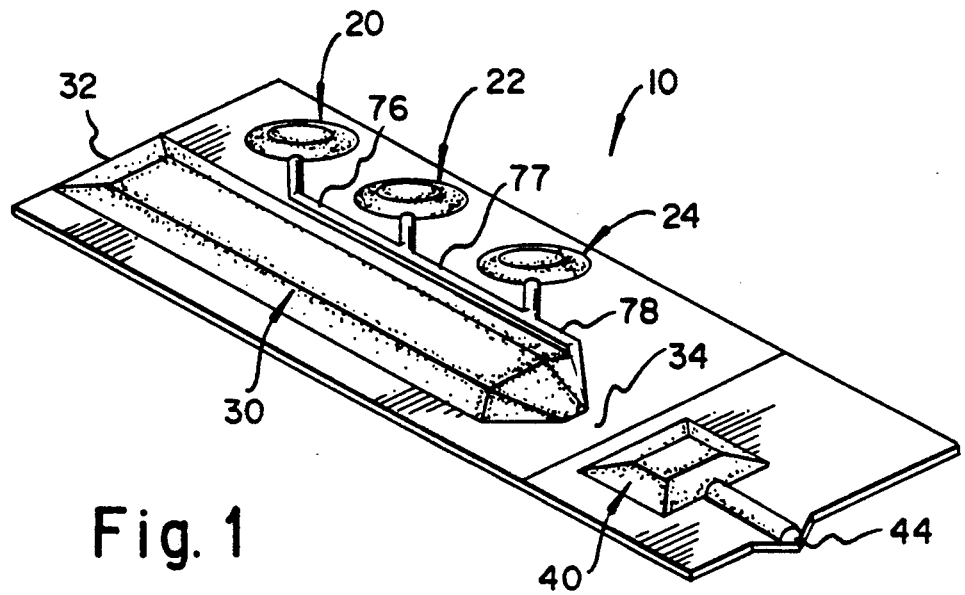
FIG. 1 is an isometric view of an extraction device constructed in accordance with the invention.
Figure 2:
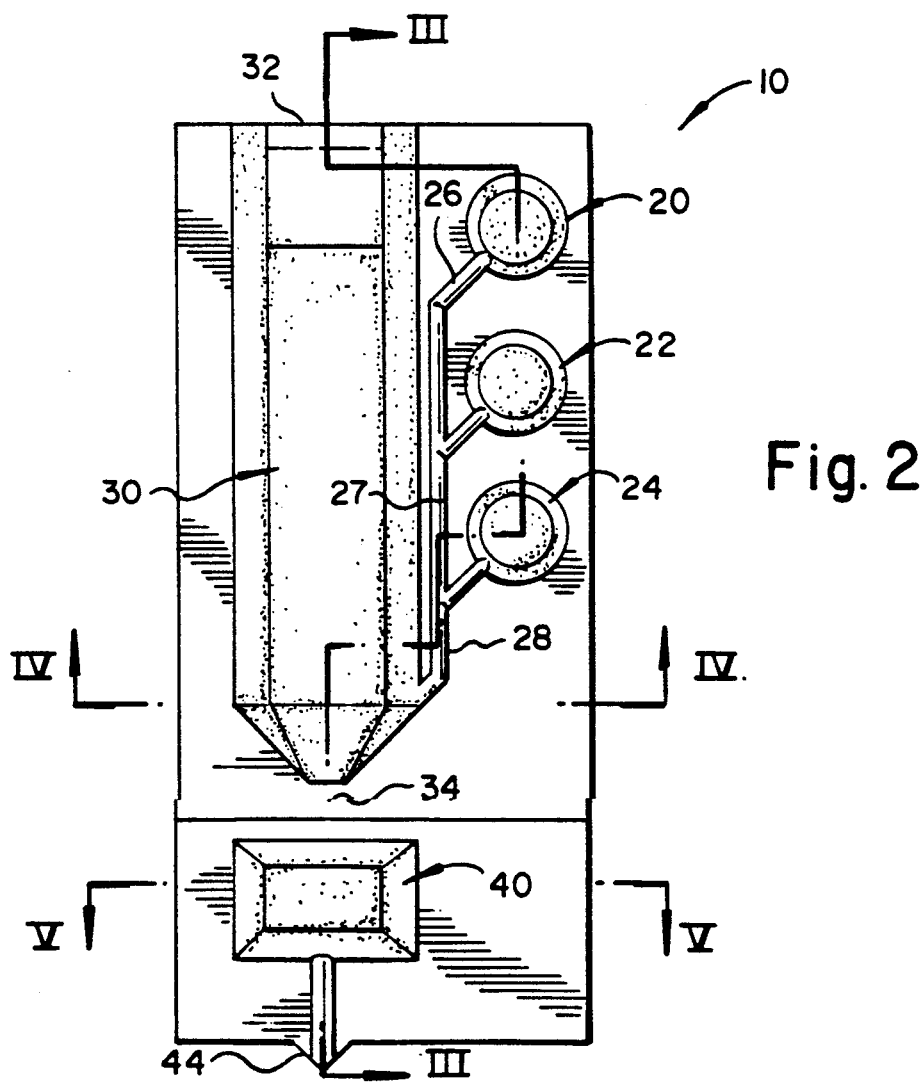
FIG. 2 is a plan view of the device of FIG. 1.

Referring to FIGS. 1 and 2, device 10 is generally flat due to its construction, and comprises enclosed compartments of which compartments 20, 22 and 24 are provided with liquid solutions, at least one of which contains a conventional extracting reagent, e.g., 1,4-dithiothreitol and a protease, for the extraction of chlamydia antigens. Compartment 30 is a reaction compartment, of which end 32 is an inlet end which receives a sample such as on a swab and is then sealed. Compartments 20, 22 and 24 have fluid passageways 26, 27 and 28, FIG. 2, leading to compartment 30, except that a temporary, burstable blocking member is provided to block flow until it is desired, as discussed below An exit passageway 34 is provided at the end of compartment 30 opposite to end 32, which is also temporarily blocked, as described below. Once unblocked, passageway 34 fluidly connects with a chamber 40 that contains a filter 42, FIG. 3, and an exit aperture 44 is located downstream of the filter. In accordance with one option of the invention, aperture 44 allows flow out of device 10 into some other apparatus, not shown.

Figure 3:
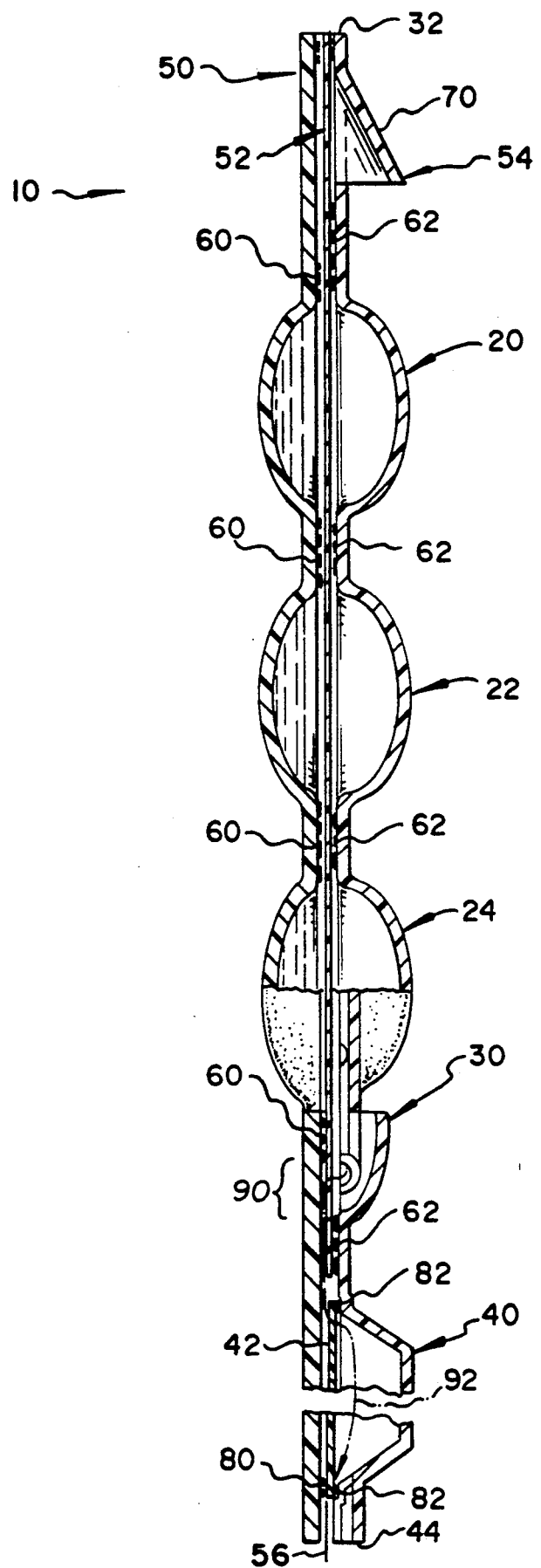
FIGS. 3 and 4 are section views taken along the lines III—III and IV—IV, respectively, of FIG. 2.
Figure 4:
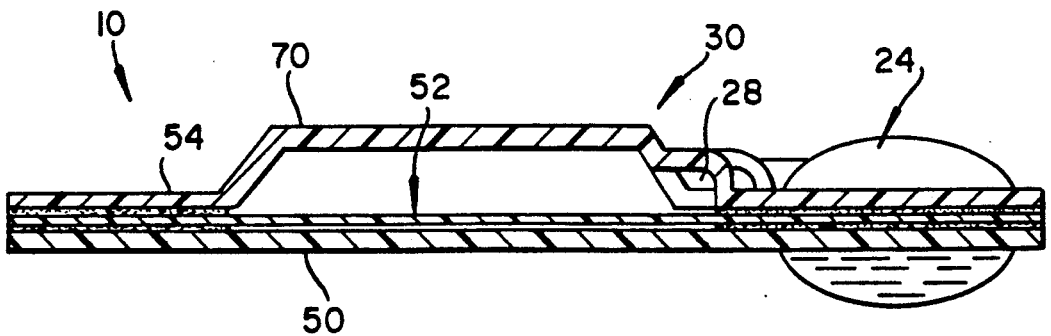
Figure 5:
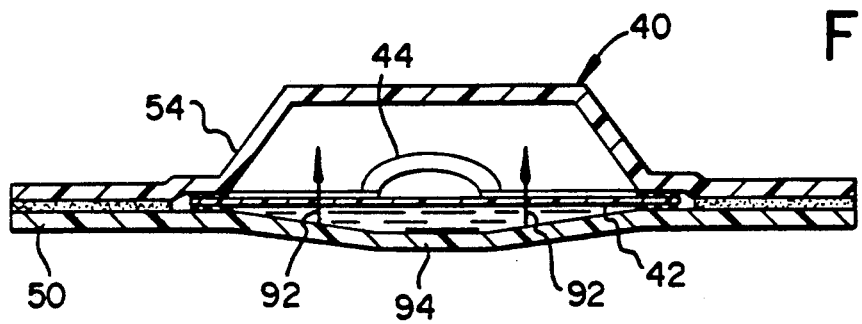
FIG. 5 is a section view taken along the line V—V of FIG. 2, after the thin separation wall x has burst and prior to the liquid passing through the filter, arrow y.

The construction of the temporary blocking means is better understood by reference to FIGS. 3-5. Thus, FIG. 3, each compartment 20-24 is formed by preferably plastic sheets 50, 52 and 54. First sheet 50 is an exterior, relatively thick sheet, preferably formed to provide approximately half of the "bubbles" used to delimit the compartment volume. Second sheet 52 is relatively thin and extends preferably along the median plane 56 of device 10, and divides and separates into two parts the volume of each compartment 20, 22 and 24 so as to temporarily keep the pre-incorporated liquids between sheets 50 and 52. As used herein, "relatively thin" or "thinner" means, in comparison to sheets 50 and 54, and refers to a relative thinness that is sufficient to cause sheet 52 to tear or burst, before any other part of the compartment fails, when exterior pressure is applied. A preferred relative thinness is one-fifth the thickness of sheets 50 and 54, and no more than about 0.15 mm in thickness.

Sheet 54 is generally a mirror image of sheet 50, at least with respect to compartments 20, 22 and 24.

The sheets are laid down flat and sheet 52 is sealed, preferably by heat-sealing, to sheets 50 and 54 at 60 and 62, respectively, to provide the temporary division of volumes as described. These seals extend around the perimeter of compartments 20, 22 and 24.

Figure 7:
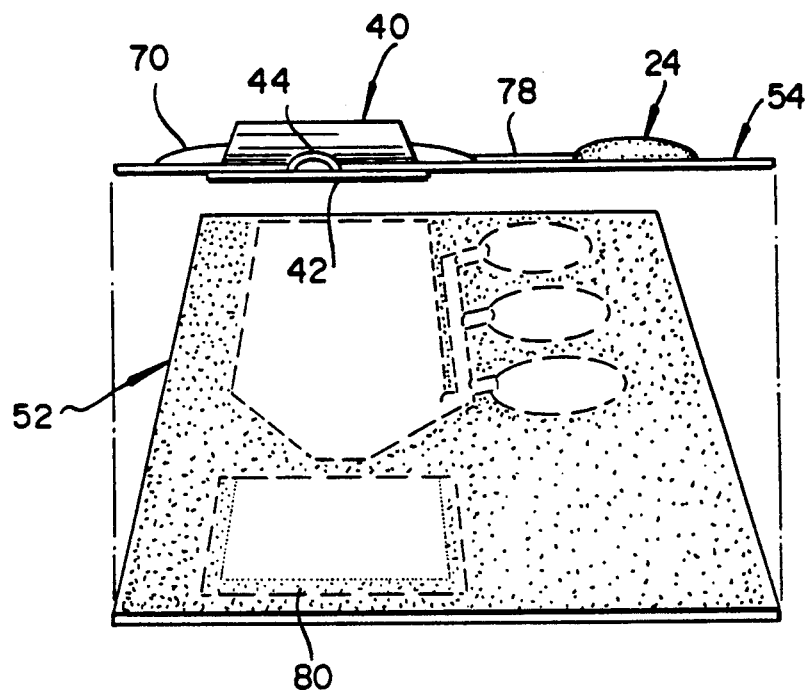
FIG. 7 is an exploded, partially isometric view illustrating a later step in the manufacture of the device.

Regarding reaction compartment 30, that is initially formed as a blister 70, FIG. 7, in sheet 54 by sealing sheet 54 around the perimeter of compartment 30, to sheet 52. Sheet 54 also has preformed in it, blisters 76, 77 and 78, FIG. 1, for passageways 26, 27 and 28, respectively. Sealing of sheet 54 to sheet 52 occurs, FIG. 7, over the entire shaded area of sheet 52, and also the dotted area 80 to seal sheet 52 to filter 42 previously attached to sheet 54. Filter 42 is sealed to sheet 54, FIG. 3, at seal 82, which extends around the perimeter except for exit aperture 44.

Figure 6:
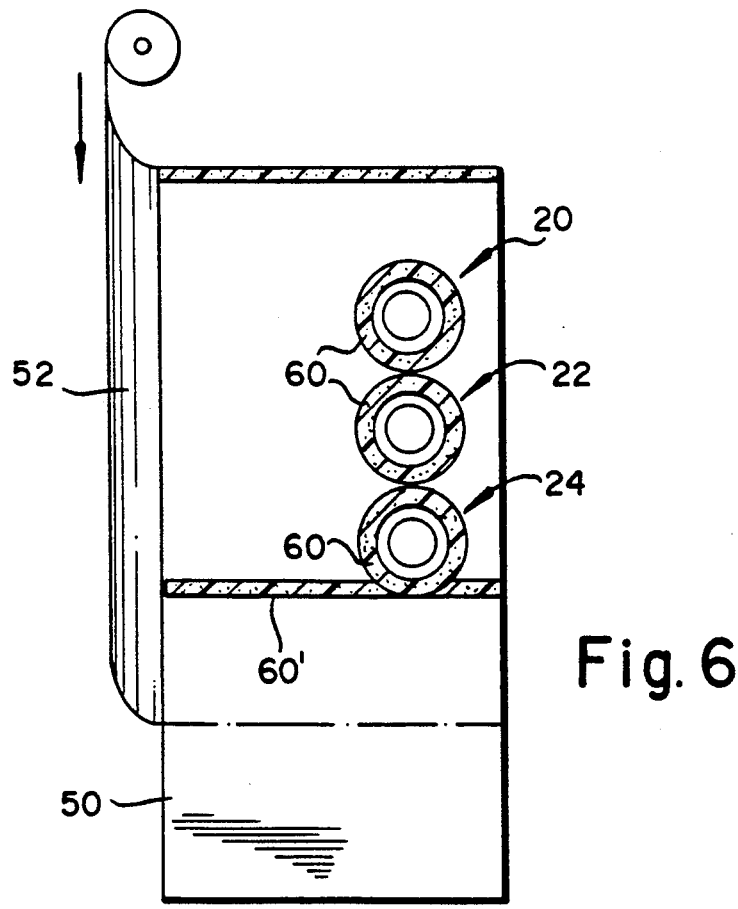
FIG. 6 is a schematic plan view illustrating an early step in the manufacture of the device.

The manufacture of device 10 will be readily apparent. Sheet 50 is formed first, and liquids added to the blisters. Sheet 52 overlies the liquid and sheet 50, and is sealed at seals 60 and 60', FIG. 6. Next, sheet 54 is formed with its blisters for compartments 20, 22, 24, 30 and 40, and filter 42 is sealed to sheet 54 at 82, FIG. 3, around all the perimeter of compartment 40, EXCEPT for exit aperture 44, which must be left open. Next, the subassembly comprising sheets 54 and filter 42 is joined to sheet 52 covering the liquids and the underneath sheet 50 by sealing over the shaded and dotted areas 80 of sheet 52, FIG. 7.

Most preferably, sheet 52 comprises low density polyethylene. Sheets 50 and 54 preferably are polyethylene, polypropylene laminate combinations thereof, or any similarly heat-sealable plastic.

The result is a device 10 that is open at inlet 32 and exit aperture 44, having compartments defined by a burstable sidewall 52.

In use, the sample is inserted into compartment 30 via inlet 32, which is then sealed. Reagents are then moved into compartment 30 as needed from compartments 20, 22 and 24 by selectively bursting the latter. This is achieved by applying external pressure to sheet 50 at the compartment that is to be burst. Because sheet 52 is the weakest part of the compartment, and is weaker than all of the seals between the sheets described above, bursting occurs through sheet 52 and not anywhere else. Flow then proceeds into compartment 30, preferably by maintaining device 30 vertical or, at least, slightly vertical out of the horizontal plane, with inlet 32 up.

To obtain flow from compartment 30 through filter 42, pressure is applied to blister 70. This causes sheet 52 to fail in the area 90, FIG. 3, between seals 60 and 62, and flow then proceeds through filter 42 into compartment 40 and out aperture 44, arrow 92 (also shown in FIG. 5). Sheet 50 preferably flexes out at 94, FIG. 5, when flow occurs at area 90.

Optionally, sheet 50 can be permanently thermoformed with bulge 94, FIG. 5, instead of flexing to form it as needed.

Optionally, FIGS. 8 and 9, the exit aperture emptying the filter compartment can lead directly to a test area that is incorporated into the device itself. Parts similar to those previously described bear the same reference numeral to which the distinguishing suffix "A" is appended.

Thus, device 10A comprises reaction compartment 30A, and compartments 20A, 22A, and 24A, FIG. 9, feed into end 34A of the compartment 30A and then into filter compartment 40A that includes filter 42A, FIG. 9, all as before. However, exit aperture 44A, FIG. 8, feeds into a fluid passageway 100 formed as part of sheet 54A, which leads to a detection compartment 110. Also, feeding into passageway 100 are at least two, and preferably three, other burstable compartments 102, 104 and 106 via passageways 108, FIG. 9. The latter compartments are formed substantially identically to compartments 20A, 22A and 24A, as described above and are temporarily covered by sheet 52A—see FIG. 9. That is, liquid reagents enter passageways 108 and 100 only by bursting relatively thin sheet 52A, FIG. 9, by applying exterior pressure to the respective compartment.

Detection compartment 110 can have any convenient detection chemistry which depends, of course, on the antigen of interest. For example, three areas of detection 112, 114 and 116 can be provided to detect a negative control, the sample and a positive control, respectively. The chemistries for areas 112, 114 and 116 can be, for example, those used in the "SureCell"® test device available from Eastman Kodak Company for chlamydia assays.

Either of the embodiments described above is preferably substantially flexible; that is, it can be bent out of the median plane 56, FIG. 3, by manual grasping alone, and twisting. The structure that allows this is the parallel overlaying of sheets 50, 52, and 54, and their sealing together to form a device that is much thinner than it is long or wide, and the absence of rigid cross-braces joining these sheets together. Such flexibility is advantageous in that it allows manipulation of any swab that is placed and sealed inside chamber 30—a step that is needed to aid in mixing the reagents with the swab.

Figure 10:
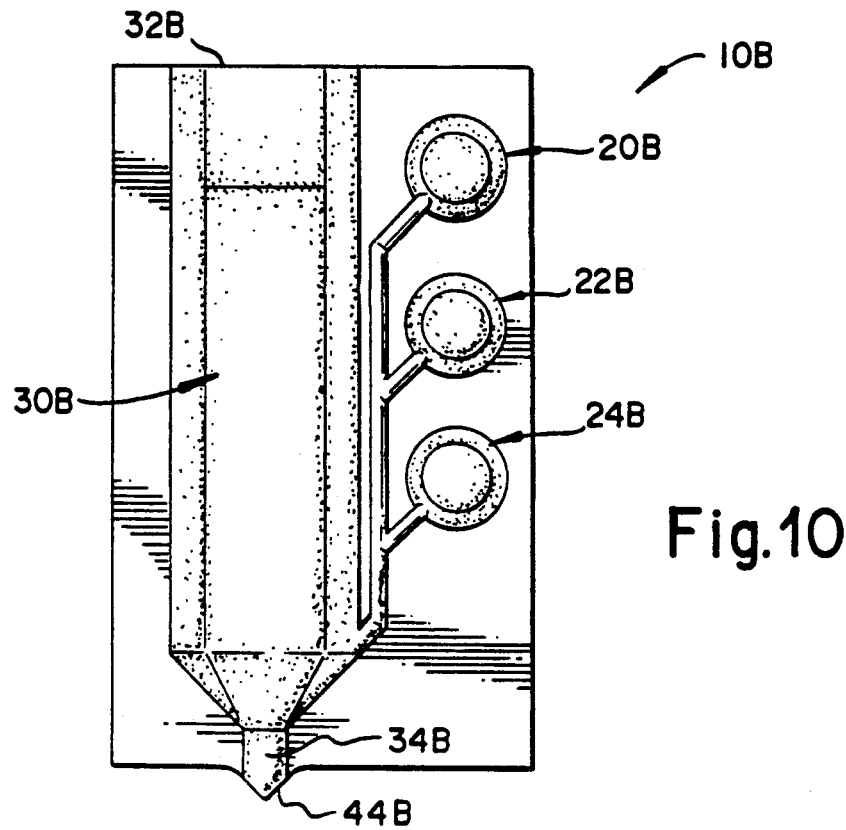
FIG. 10 is a plan view similar to FIG. 2, except it illustrates yet another alternate form of the invention.

It is not required that the device of the invention always incorporate a filter to filter out the extracted antigens from extraneous matter. Instead, FIG. 10, the filter can be omitted, whether or not a detection compartment is integral with the extraction compartment. Parts similar to those previously described bear the same reference numerals, to which the distinguishing suffix "B" is appended.

Thus, device 10B comprises reaction compartment 30B, and compartments 20B, 22B, and 24B feed into compartment 30A and then out end 34B; all as before. However, end 34B feeds to exit aperture 44B without passage through a filter. (Optionally, not shown, exit 44B can feed directly into an integrally attached detection compartment as in the embodiment of FIG. 9.)

Such a filterless embodiment is useful, e.g., when testing a herpes sample that is swabbed from a patient sore and then deposited onto a culture. Subsequently, the cultured growth is then swabbed, and it is this swab that is inserted into compartment 30B to provide the source of the sample.

Figure 11:
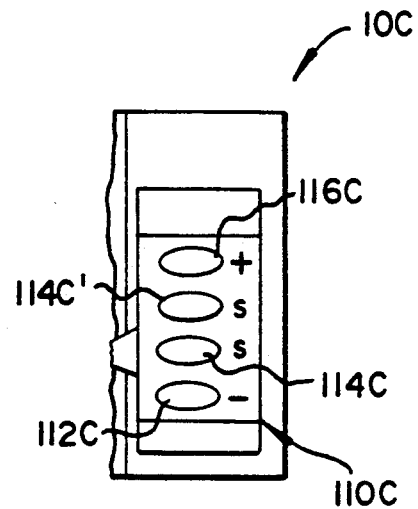
FIG. 11 is a fragmentary section view similar to that of FIG. 9, but of another alternate embodiment of the invention.

Yet another option is that the integral detection compartment can detect more than one analyte, FIG. 11, by having more than one patient sample area. Parts similar to those previously described bear the same reference numeral to which the distinguishing suffix "C" is appended. Thus, device 10C is identical to that shown in FIGS. 8 and 9, for example, except that detection compartment 110C has two sample areas of detection 114C and 114C', to test for, e.g., the multiple antigens of periodontal assays, or chlamydia and herpes. In place of the symbols "S", one can use instead, e.g., "C" and "H", respectively, in the case of chlamydia and herpes.

The invention has been described in detail with particular reference to preferred embodiments thereof, but it will be understood that variations and modifications can be effected within the spirit and scope of the invention. For example, although other features can be added besides those described, it is also useful free of any other features. That is, it can consist of only the enumerated parts.

What is claimed is:

1. A generally flexible extraction device containing a predisposed reactant, comprising
    first and second plastic sheets superimposed and sealed together by first seal means to comprise a spaced compartment, a reagent in said compartment, said second sheet being thinner and more burstable than said first sheet so as to allow rupturing of said compartment through said second sheet at a predictable force, a third plastic sheet attached by second seal means to said first two sheets with said second sheet being between, and generally parallel to, said first and third sheets, said second sheet being unsupported at said compartment other than at said first and said second seal means, so as to expand and burst upon an applied external pressure, said third sheet being formed so as to be spaced away from said first and second sheets adjacent to said compartment and to comprise a reaction chamber and inlet means for introducing a specimen between said third and second sheets to said reaction chamber, an exit aperture, and a flow path for liquid extending between said second and third sheets and between said inlet means and said exit aperture,
    each of said seal means being stronger than the burst strength of said second sheet.

2. A device as defined in claim 1, and further including a filter extending across said flow path between said first and third sheets,
    and third seal means across said flow path in between said filter and said compartment, formed between said second and third sheets so as to temporarily isolate said filter from liquid flowing out of said reaction chamber.

3. A device as defined in claim 2, wherein said second sheet terminates at said third seal means and said flow path continues between said first and third sheets only, through said filter.

4. A device as defined in claim 1, wherein said first sheet is flexible at the location of said second seal means so that said first sheet flexes when said second sheet bursts to allow liquid flow between said first and third sheets.

5. A device as defined in claim 2, wherein said exit aperture is immediately downstream of said filter.

6. A device as defined in claim 2, and further including a detection compartment within said device and fluidly connected to said exit aperture, so that passage of liquid through said filter is followed by flow of the filtered liquid into said detection compartment.

7. A device as defined in claim 1, wherein said second sheet is approximately one-fifth the thickness of said first sheet.

8. A device as defined in claim 1, wherein said second sheet comprises polyethylene and said first, second and third seal means are heat-seals.

9. An integrated extraction and immunoassay device comprising
    an extrusion portion comprising a first burstable compartment temporarily confining extracting reagent preincorporated therein, said first compartment comprising first and second sheets superimposed and sealed together by first seal means, said second sheet being thinner than said first sheet to expand and burst under an applied external pressure, a third sheet attached by second seal means to said first and second sheets with said second sheet being between said first and third sheets, said second and third sheets defining a second reaction compartment having a temporarily sealed exit, said second sheet being unsupported other than at said first seal means and said second seal means and providing a fluid passageway from said first compartment and said second compartment when said second sheet is burst,
    and an immunoassay test device integrally attached to said extraction portion and comprising a detection compartment in fluid communication with said temporarily sealed exit upon the unsealing of said exit.

10. An integrated device as defined in claim 10, wherein said detection compartment includes plural sites attached to a sidewall therein each site specific to a different analyte.

11. In a method of bursting a burstable compartment in an extraction device to advance a liquid, said extraction device comprising a first compartment temporarily confining liquid therein, said first compartment comprising first and second sheets superimposed and sealed together by a first seal and a third sheet attached by a second seal to said first and second sheets with said second sheet being between said first and third sheets, said second and third sheets defining a second compartment, and then applying external pressure sufficient to burst the liquid out of the compartment, but not out of the device;

the improvement comprising providing as said second sheet, an unsupported sheet material substantially thinner than the material of said first and third sheets, the material of said second sheet having a thinness sufficient to cause said second sheet to burst under application of external pressure before said first seal or said second seal bursts, so that said bursting occurs predictably through said second sheet at a predetermined burst force, and not through said first seal or said second seal.

12. A method as defined in claim 11, wherein said second sheet comprises a sheet having approximately one-fifth the thickness of the material of said first and third sheets.

13. A method as defined in claims 11 or 12, wherein said second sheet comprises a polyethylene sheet and said seals are heat-seals.

14. A method as defined in claim 11, wherein said device is manually flexible, and further including the subsequent step of twisting the device at at least one of the compartments to manipulate the liquid to aid in mixing.

* * * * *